United States Patent [19]

Kuhn

[11] Patent Number: 4,643,675

[45] Date of Patent: Feb. 17, 1987

[54] DENTAL HANDPIECE

[75] Inventor: Bernhard Kuhn, Schemmerhofen, Fed. Rep. of Germany

[73] Assignee: Kaltenbach & Voigt GmbH & Co., Biberach an der Riss, Fed. Rep. of Germany

[21] Appl. No.: 757,090

[22] Filed: Jul. 19, 1985

[30] Foreign Application Priority Data

Sep. 14, 1984 [DE] Fed. Rep. of Germany ....... 3433877

[51] Int. Cl.[4] .............................................. A61C 1/08
[52] U.S. Cl. ..................................... 433/126; 433/105
[58] Field of Search ................ 433/126, 130, 105, 114

[56] References Cited

U.S. PATENT DOCUMENTS

| | | | |
|---|---|---|---|
| 4,213,756 | 7/1980 | Reich et al. | 433/126 |
| 4,245,985 | 1/1981 | Eibofner et al. | 433/126 |
| 4,260,381 | 4/1981 | Eibofner et al. | 433/126 |
| 4,310,310 | 1/1982 | Bailey | 433/126 |
| 4,382,790 | 5/1983 | Loge et al. | 433/126 |
| 4,406,621 | 9/1983 | Bailey | 433/126 |
| 4,504,227 | 3/1985 | Lohn | 433/126 |

FOREIGN PATENT DOCUMENTS

| | | | |
|---|---|---|---|
| 1219170 | 1/1967 | Fed. Rep. of Germany | 433/126 |
| 1566291 | 10/1980 | Fed. Rep. of Germany | 433/128 |
| 2644458 | 6/1981 | Fed. Rep. of Germany | 433/105 |

Primary Examiner—John J. Wilson
Attorney, Agent, or Firm—Scully, Scott, Murphy & Presser

[57] ABSTRACT

A dental handpiece, encompassing a gripping sleeve and a head sleeve which is bent relative to the longitudinal axis of the gripping sleeve, as well as a drive shaft which is supported within the handpiece and which drives a treating implement arranged in a head at the free end of the head sleeve. The drive shaft is transversely divided in the region of the bending location, wherein the two drive shaft parts are in interengagement through the intermediary of a follower or engaging device, and wherein a planetary ball gear drive is interposed in the driven drive shaft part. While retaining the planetary ball gear drive which acts as safeguard against overloads, it is possible, without an exchange of the complete handpiece, to effect in a rapid and simple manner a transition to working with a certain head which is selected from a large number of heads.

14 Claims, 2 Drawing Figures

DENTAL HANDPIECE

BACKGROUND OF THE INVENTION

1. Field of the Invention

The present invention relates to a dental handpiece, encompassing a gripping sleeve and a head sleeve which is bent relative to the longitudinal axis of the gripping sleeve, as well as a drive shaft which is supported within the handpiece and which drives a treating implement arranged in a head at the free end of the head sleeve, the drive shaft being transversely divided in the region of the bending location, wherein the two drive shaft parts are in interengagement through the intermediary of a follower or engaging device, and wherein a planetary ball gear drive is interposed in the driven drive shaft part.

2. Discussion of the Prior Art

Handpieces of that type are connected to a drive component at the free end of the gripping sleeve somewhat of the type as disclosed in German Pat. No. 12 19 170, so as to be easily detachable. The inventively provided planetary ball gear drive disclosed in the present application, in contrast with other types of drives, for example, a worm gear drive which is known from the disclosure of German AS No. 15 66 291 and which restricts the view of the treating area, forms a safeguard against overloads which is afforded through the use of simple means.

A handpiece of the above-mentioned type is known from the disclosure of German AS No. 26 44 458. In this known handpiece, the planetary ball gear drive of the driven drive shaft part is located in the region at the end of the head sleeve towards the gripping sleeve, and thereby in the region of the bending location of the handpiece, whereby the head sleeve and the gripping sleeve are interconnected by means of a screw-threaded arrangement which, for example, for mounting purposes, are only detachable with difficulty, and as result cannot be manipulated by personnel in the dental practice. In addition thereto, the location of the planetary ball gear drive in the region of the bending location prohibits any detaching between the head sleeve and the gripping sleeve, inasmuch as through such a detaching there would be eliminated the stable engaging relationships of the planetary ball gear drive, as well as the correct association of the drive component, for instance, during the reestablishing of the connection, and thereby produce operational malfunctions of the drive system. It is a frequent occurrence that, because of reasons required by the driving operation and treatment, it is necessary to work with another, for example, smaller head. Heretofore, in order to facilitate the foregoing, inasmuch as the mentioned head sleeve and gripping sleeve are practically inseparable, the entire handpiece had to be detached from the drive component and then exchanged for another complete handpiece which incorporates the desired other head. Consequently, there is obtained a complex bearing support.

SUMMARY OF THE INVENTION

The present invention, as can be readily ascertained, has as its object to provide a dental handpiece of the above-mentioned type where, while retaining the planetary ball gear drive which acts as safeguard against overloads, it is possible, without an exchange of the complete handpiece, to effect in a rapid and simple manner a transition to working with a certain head which is selected from a large number of heads.

The advantages which are achieved by the present invention can now be essentially ascertained in that due to the quick-action coupling it is possible to provide an easy and rapid separation and joining together of the head sleeve and gripping sleeve, and essentially, due to the position of the planetary ball gear drive which is secured against any release of the drive engagement proximate the free end of the head sleeve, without any danger of an operational malfunction of the planetary ball gear drive.

BRIEF DESCRIPTION OF THE DRAWINGS

Further advantages, features and modifications of the invention may now be ascertained from the following description of exemplary embodiments thereof, taken in conjunction with the accompanying drawings; in which.

DETAILED DESCRIPTION

Figure 1:
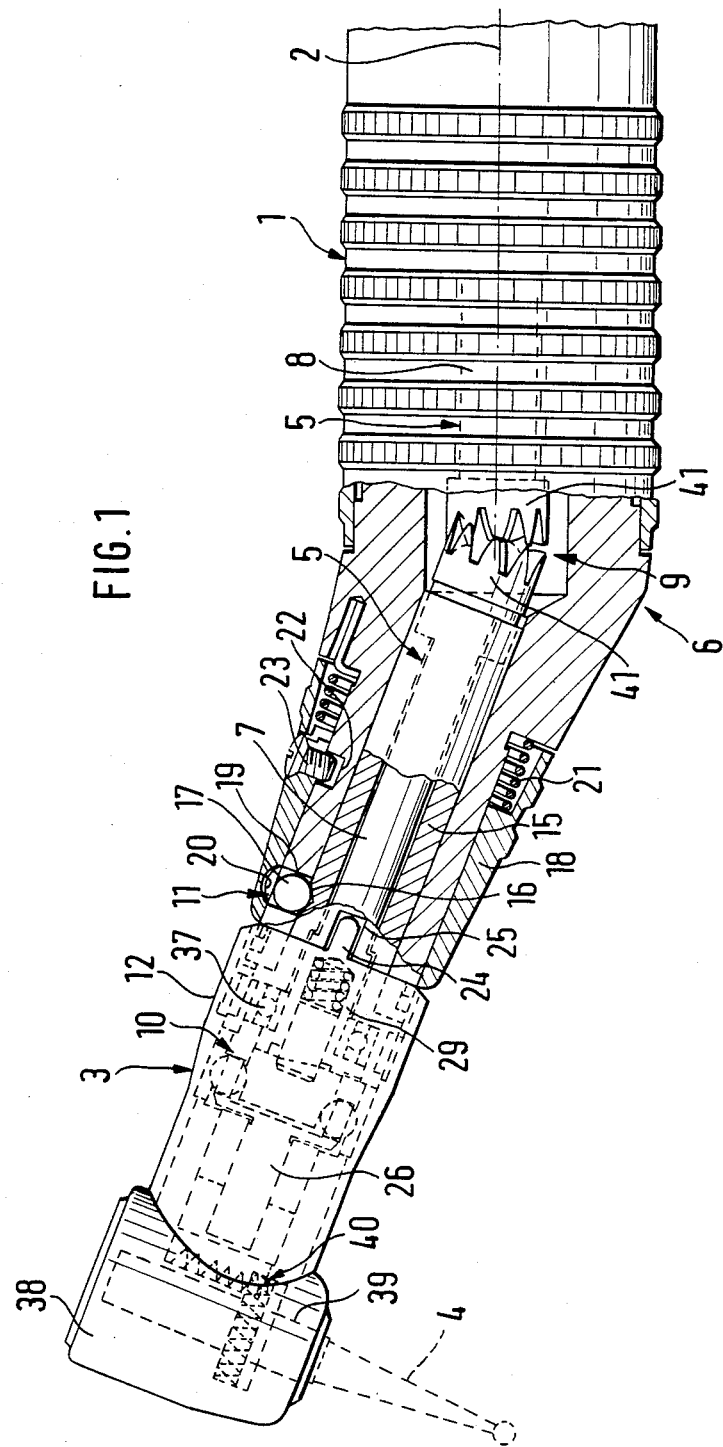
FIG. 1 illustrates a side view, partly in section, of a dental handpiece.

The dental handpiece encompasses a gripping sleeve 1 and a head sleeve 3 which is bent relative to the longitudinal axis of the gripping sleeve 2 at an obtuse angle, as well as a drive shaft 5 which is supported in the handpiece and which drives a treating implement 4 arranged in a head 38 at the free end of the head sleeve 3. The drive shaft 5 is transversely divided in the region of the bending location 6, whereby the two such formed drive shaft parts 7, 8 are engagement with each other through a follower or engaging arrangement 9, and whereby the driven drive shaft part 7 has a planetary ball gear drive 10 interposed therein, so that there is formed a shaft section 26 of the driven drive shaft part 7 remote from the gripping sleeve, and a shaft section 29 of the driven drive shaft part 7 proximate the gripping sleeve.

The planetary ball gear drive 10 of the driven drive shaft part 7 is located in the region of the free end or in proximity to the head 38 of the head sleeve 3, whereby the head sleeve is easily connectable with or detachable from the gripping sleeve 1 through a quick-action coupling 11.

The quick-action coupling 11 consists of engaging means 16 on the head sleeve 3 and complementary engaging means 17 on the gripping sleeve 1. The planetary ball gear drive 10 is arranged in a reinforced or heavier head sleeve part 12 which includes a through-opening 13 for stop plate 14 towards the gripping sleeve for the driven drive shaft part 7. Extending from the stop plate 14 is a thinner head sleeve part 15 which receives the driven drive shaft part 7 and which is axially insertable into the gripping sleeve 1, which is provided on its outside with engaging means 16 belonging to the quick-action coupling 11, and which can be brought into engagement with complementary engaging means 17 on the gripping sleeve 1 which also belong to the quick-action coupling. Hereby, there is created the capability that, in a particular simple manner, this assists in the maintenance of the appropriate engaging relationships of the planetary ball gear drive 10 during the separation of the gripping sleeve 1 and the head sleeve 3.

The engaging means 16 is formed through one or more detents in the outside of the thinner head sleeve part 15, and the complementary engaging means 17 by a clamping ball. Arranged on the gripping sleeve 1 is a turning sleeve 18 for bringing the clamping ball into and out of engagement with the detent. The clamping ball is located in a cutout 19 in the gripping sleeve 1. For the engagement with the clamping ball, there is worked into the inner wall of the turning sleeve 8 a recess 20, which is generally partly-circular in cross-section and which contacts the clamping ball, and whose depth reduces more less gradually towards at least one of its ends. The turning sleeve 18 has a resetting member 21 associated therewith which seeks to maintain the forms in a rotational position corresponding to the engaged position of the clamping ball. During the rotation of the turning sleeve 18 against the resetting force of the resetting member 21, the clamping ball moves out of the recess 20 forming the engaging means 16, so that the quick-connect coupling 11 is released and the head sleeve 3 can be pulled off. During the insertion of the thinner head sleeve portion 15 of another head sleeve 3 into the gripping sleeve 1, the turning sleeve 18 is retained in the above-mentioned turned rotational position. After the effected insertion, the turning sleeve 18 is released so as to rotate under the effect of the resetting member 21 into a rotational position in which the clamping ball is brought into engagement with the recess and latched therein, and thereby the quick-connect coupling 11 maintained in the coupling position.

The resetting member 21 is formed by a helical torsion spring which encompasses the gripping sleeve, whose one end is fastened to the gripping sleeve 1 and whose other end is fastened to the turning sleeve 18. For securing its axial position, the inner wall of the turning sleeve 18 possesses a guide pin 23 which projects inwardly into an outer circumferential groove 22 on the gripping sleeve 1. The circumferential groove 22 only needs to extend over such a portion of the circumference which corresponds to the required extent of rotation of the turning sleeve 18.

As can be further ascertained from the drawing, for the mutual engagement of the gripping sleeve 1 and the head sleeve 3 secured against rotation in a rotational position ensuring the mutual engagement between the engaging means 16 and the complementary engagement means 7, the sleeves are provided in the region of their mutually facing end surfaces, relative to the applicable sleeve axis, with eccentrically located latching means 24 and complementary latching means 25. The latching means 24 are constructed as axially projecting protuberances and the complementary latching means 25 as axially retracted niches. There are presently provided two protuberances and two niches which are arranged so as to be presently offset by 180°.

The end of the shaft section 26 of the driven drive shaft part 7 remote from the gripping sleeve, which faces the planetary ball gear drive 10, is formed as a type of open cage in the shape of a rounded fork or slotted jaw, whereby the axially extending cage rods or tines 27 engage intermediate the balls 28 of the planetary ball gear drive 10. The balls 28 hereby supported under a frictional contact between the circumference of the end of the shaft section 29 of the driven drive shaft part 7 towards the gripping sleeve and a non-rotatable annular track 30 fastened to the head sleeve. Hereby, the annular track 30 is formed by the inner wall of a separate ring 30a which is fastened to the head sleeve.

One of the two shaft sections 26, 29; in effect, the shaft section 29 towards the gripping sleeve, possesses an adjusting or positioning device 31 which acts on the balls 28 of the planetary ball gear drive 10. Hereby, the cage rods or tines 27 are located on the shaft section 26 which is remote from the gripping sleeve.

For the formation of the adjusting device 31, the shaft section 29 towards the gripping sleeve is transversely divided, whereby the mutually facing ends of the thus formed two shaft section portions contact against each other by means of cooperating positioning cam surfaces 32 acting in similar inclined planes. Hereby, there is additionally provided a compensating spring 33 for reducing the contact pressure of the ends of the two mentioned shaft section portions, which is constituted of a helical compression spring. The compensating spring 33 is arranged in a blind bore 34 in the end surface of the shaft section shown towards the right in the drawing. The circumferential section of the shaft section portion of the shaft section 29 remote from the gripping sleeve, against which their contacts the balls 28 of the planetary ball gear drive 10, possesses a conical annular section and which comes into positioning cooperation with the balls 28 under the effect of the adjusting or positioning device 31.

Figure 2:
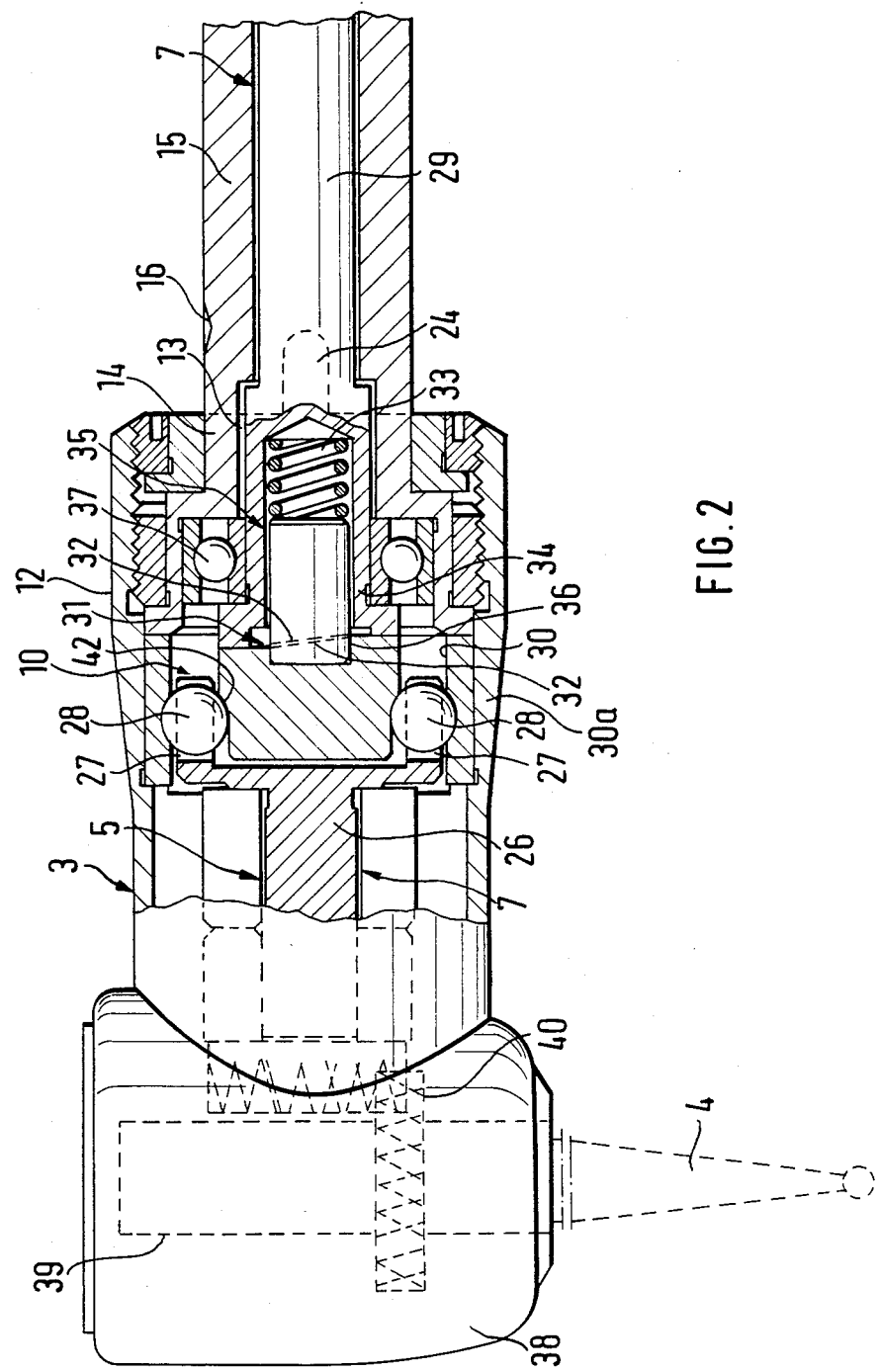
FIG. 2 illustrates a sectional view of the head sleeve of the dental handpiece of FIG. 1, partly in a side view, and shown on an enlarged scale.

There is additionally provided a centering device 35 which axially aligns the two shaft section portions, which is constituted, for one part, of a blind bore 36 in the one end surface in the one shaft section portion which receives the compensating spring 33, and for the other part, a centering pin which projects into a blind bore 36 in the end surface of the other shaft section portion. The compensating spring 33 hereby exerts a pressure against the centering pin forming the centering device 35, and presses the pin against the shaft section portion of the shaft section 29 towards the gripping sleeve, as shown in the left in FIG. 2.

The end of the shaft section remote from the gripping sleeve; in effect, in the drawing the left end of the shaft section portion facing the gripping sleeve of the shaft section towards the gripping sleeve, is supported in the heavier head sleeve portion 12 with the aid of a ball bearing 37.

The treating implement 4 is inserted into a drive sleeve 39 which is supported within the head 38 of the head sleeve 3, and which is set into rotation through a gear drive 40 by the driven drive shaft part 7.

The follower or engaging device 9 consists of mutually interengageable drive gears 41 which are arranged on the mutually facing ends of the driven drive shaft part 7 and the driving drive shaft part 8.

What is claimed is:

1. In a dental handpiece, including a gripping sleeve and a head sleeve bent relative to the longitudinal axis of said gripping sleeve; a head for a treating implement in said head sleeve; a drive shaft for driving a treating implement being arranged within said head at the free end of the head piece and supported in the handpiece, said drive shaft being transversely divided in the region of the bend between said sleeves, follower means for engaging the two parts of the drive shaft with each other; and a planetary ball gear drive being interposed in the driven drive shaft part in the region of the free end of the head sleeve, the improvement comprising: a quick-connect coupling for connecting said head sleeve with said gripping sleeve, including engaging means on the head sleeve and complementary engaging means onthe gripping sleeve, said planetary ball gear drive being located in a reinforced section of the head piece having a through-opening for a stop plate towards the gripping sleeve on the driven drive shaft part, a thinner head sleeve section for receiving the driven drive shaft part extending from said stop plate and being axially insertable into the gripping sleeve, the exterior of said thinner head sleeve section including engaging means forming a part of the quick-connect coupling which is engageable with complementary engaging means on the gripping sleeve forming a further part of said quick-connect coupling, the end of one shaft section of the driven drive shaft part towards the planetary ball gear drive including an open cage in the shape of a circular forked member, the fork tines of said cage engaging between the balls of the planetary ball gear drive, wherein the balls are supported under frictional engagement between the circumference of the end of the other shaft section of the driven drive shaft part and a non-rotatable annular track, one of the two shaft sections including positioning means acting on the balls of the planetary ball gear drive, said positioning means being arranged on the shaft section towards the gripping sleeve, and the cage fork tines on the shaft section remote from the gripping sleeve, said shaft section being transversely divided to form said positioning means, and the facing ends of the resultingly formed shaft section parts are located opposite each other through cooperating positioning cam surfaces.

2. A handpiece as claimed in claim 1, wherein said engaging means comprises at least one detent formed in the exterior of the thinner head sleeve section, and said complementary engaging means comprises a clamping ball; and a turning sleeve being arranged on the gripping sleeve adapted to move the clamping ball into and out of engagement with the detent.

3. A handpiece as claimed in claim 2, wherein the clamping ball forming the complementary engaging means is arranged in a cutout of the gripping sleeve.

4. A handpiece as claimed in claim 2, wherein the inner wall of the turning sleeve includes a recess partially circular in cross-section having the clamping ball contacting thereagainst, said recess being a reducing depth towards at least one end thereof.

5. A handpiece as claimed in claim 2, wherein a resetting member is associated with the turning sleeve for restraining said turning sleeve in a rotational position for effecting the engaging position of said clamping ball.

6. A handpiece as claimed in claim 5, wherein said resetting member comprises a helical spring encompassing the gripping sleeve, one end of said spring being fastened to the gripping sleeve and the other end of said spring being fastened to the turning sleeve.

7. A handpiece as claimed in claim 2, wherein said turning sleeve includes a guide pin extending inwardly from the inner wall thereof into an external circumferential groove on the gripping sleeve for securing the axial positioning of said turning sleeve.

8. A handpiece as claimed in claim 1, wherein the gripping sleeve and the head sleeve for mutual connection against relative rotation in a rotational position ensuring the mutual engagement of the engaging means and the complementary engaging means, include eccentrically located latching means and complementary latching means on their facing end surfaces, relative to the applicable sleeve axis.

9. A handpiece as claimed in claim 8, wherein the latching means comprise axially projecting protuberances and the complementary latching means comprise axially retracted niches.

10. A handpiece as claimed in claim 1, including a compensating spring for reducing the contact pressure of the ends of the shaft section parts.

11. A handpiece as claimed in claim 10, wherein the compensating spring is arranged in a blind bore in the end surface of one of said shaft section parts.

12. A handpiece as claimed in claim 1, wherein the circumferential portion of the shaft section part of the shaft section remote from the gripping sleeve contacting the balls includes a conical annular action cooperating with the balls under the section of said positioning means.

13. A handpiece as claimed in claim 1, including centering means for axially aligning one of said two shaft section parts.

14. A handpiece as claimed in claim 13, wherein said centering means partly comprises a blind bore receiving the compensating spring in the one shaft section part, and partly a centering pin received in a blind bore in the end surface of the other shaft section part.

* * * * *